United States Patent
Kantam et al.

(10) Patent No.: US 6,316,674 B1
(45) Date of Patent: Nov. 13, 2001

(54) PROCESS FOR THE PREPARATION OF ACYL AROMATIC ETHERS

(75) Inventors: Mannepalli Lakshmi Kantam; Mutyala Sateesh; Boyapati Manoranjan Choudary; Billakanti Veda Prakash; Kondapuram Vijaya Raghavan, all of Andhra Pradesh (IN)

(73) Assignee: Council Scientific and Industrial Research, Rafi Marg (IN)

( * ) Notice: Subject to any disclaimer, the term of this patent is extended or adjusted under 35 U.S.C. 154(b) by 0 days.

(21) Appl. No.: 09/538,641

(22) Filed: Mar. 30, 2000

(51) Int. Cl.$^7$ .................................................. C07C 45/00
(52) U.S. Cl. ............................................................. 568/319
(58) Field of Search ................................................ 568/319

(56) References Cited

U.S. PATENT DOCUMENTS 5,138,098 * 8/1992 Hagen et al. ......................... 568/323
5,227,529   7/1993 Neuber et al. ....................... 568/319
5,817,878 * 10/1998 Spagnol et al. ..................... 568/319
5,962,743 * 10/1999 Gruber et al. ....................... 568/319
6,121,496 * 9/2000 Gilbert et al. ........................ 568/42

FOREIGN PATENT DOCUMENTS 9748665    12/1997  (WO) .

OTHER PUBLICATIONS

English Abstract of WO 97/48665 Dated Dec. 24, 1997.
Harvey, G. et al. Performance of Zeolite Beta in Friedel–Crafts Reactions of Functionalized Aromatics.

* cited by examiner

*Primary Examiner*—James H. Reamer
(74) *Attorney, Agent, or Firm*—Ladas & Parry

(57) ABSTRACT

An improved process for the preparation of acyl aromatic ethers useful as important intermediates for drugs and pharmaceuticals by reacting an aromatic ether with an acylating agent selected from a C2–C8 acid anhydrides, employing nano- and microcrystalline zeolite beta as catalyst is disclosed.

7 Claims, No Drawings

PROCESS FOR THE PREPARATION OF ACYL AROMATIC ETHERS

FIELD OF THE INVENTION

The present invention relates to an improved process for the preparation of acyl aromatic ethers from aromatic ethers. More particularly, this invention relates to an improved process for the preparation of acyl aromatic ethers from aromatic ethers using C2–C8 acid anhydrides, acetic anhydride to benzoic anhydride as acylating agents in the presence of nano- or microcrystalline zeolite beta catalysts. Aromatic ethers are useful and important intermediates for drugs and pharmaceuticals.

This invention particularly relates to an ecofriendly process for acyl aromatic ethers from aromatic ethers using acid anhydrides as acylating agents and zeolite beta as catalyst dispensing the use of stoichiometric amounts of corrosive, toxic aluminium chloride and hydrogen fluoride as Friedel-Crafts reagents.

BACKGROUND OF THE INVENTION

Conventional processes for the acylation of aromatic compounds, in particular the ethers of phenols consist of carrying out a Friedel-Crafts acylation reaction. The aromatic compound is reacted with an acylation agent in the presence of aluminium chloride The inherent disadvantages in the use of conventional Lewis acid metal chlorides for Friedel-Crafts acylation are that they are non-regenerable and require more than stoichiometric amounts because of strong complexation with the carbonyl product formed. Work-up to decompose the resultant intermediate complex by hydrolysis forms a large amount of waste product and separation of the product involves lengthy, cumbersome and expensive procedure.

Reference may be made to a publication by Choudary et al., Applied Catalysis A; 171,159, 1998 wherein aromatic ethers are acylated with acid anhydrides in the presence of metal ion exchanged clays with moderate yields. The drawbacks are that the conversions are moderate with low space time yields.

Reference may be made to a U.S. Pat. No. 4,960,943 wherein a process for the acylation of anisole with acid anhydrides in the presence of zeolite catalysts is disclosed. The drawbacks in this process are moderate yields and the reaction is carried out at high temperatures and pressures.

Reference may be made to a publication by Gaare et al. Journal of Molecular Catalysis, 109, 177, 1996 wherein anisole is acylated by acetyl chloride and acetic anhydride by modified zeolites.

Reference may be made to a U.S. Pat. No. 5,817,878 wherein substituted aromatic ethers, in particular anisole is acylated with an acylating agent in the presence of zeolite beta catalyst.

Reference may be made to a U.S. Pat. No. 6,013,840 wherein substituted aromatic ethers, in particular veratrole and anisole are acylated with an acylating agent in the presence of a Y zeolite, dealuminated and metal exchanged Y zeolite and $H^+$-zcolite beta catalyst.

Although the above inventions afforded good selectivity and activity, the object of the present invention is to devise a catalyst of enhanced activity and higher space time yields to reduce the capital and operative costs.

OBJECTS OF THE INVENTION

The main object of the present invention is to provide an improved process for the preparation of acyl aromatic ethers which are important intermediates for drugs and pharmaceuticals by reacting an aromatic ether selected from anisole, veratrole and ethyl phenyl ether with C2–C8 acid anhydrides as acylating agents employing nano- or microcrystalline zeolite beta as catalyst, in a stirred batch reactor or a continuous fixed bed reactor at temperatures in the range of 60–165° C. for a period of 224 h, and separating the acyl aromatic ethers by a conventional method, which obviates the drawbacks as detailed above.

It is another object of the invention to provide a process for the preparation of acyl axiomatic ethers that is safe and environmentally friendly.

It is another object of the invention to provide a process for the preparation of acyl aromatic ethers that eliminates the use of corrosive and stoichiometric amounts of aluminium chloride.

It is a further object of the invention to provide a process for the preparation of acyl aromatic ethers wherein the yields are quantitative.

It is yet another object of the invention to provide a process for the preparation of acyl aromatic ethers wherein the reactions are faster and of shorter duration.

It is a further object of the invention to provide an economical process for the preparation of acyl aromatic ethers.

Another object of the present invention is to, provide a process for the preparation of acyl aromatic ethers wherein nano- or microcrystalline zeolite beta are used as catalysts.

Another object of the present invention the particle size of nano crystalline or microcrystalline zeolite beta are 10 nm to 100 nm and 1 $\mu$m to 50 $\mu$m.

Another object of the present invention is the use of nano- or microcrystalline zeolite beta for enhanced activity as evident through higher space time yields.

Another object of the present invention is the use of nano- or microcrystalline zeolite beta for high space time yields to reduce capital investment by 20–30%.

Another object of the present invention is acylation conducted both on a batch mode in a stirred reactor and on a continuous mode in a fixed bed reactor.

Another object of the present invention is the option of continuous mode in a fixed bed reactor to save time spent on charging the reactant into the reactor, discharging the reaction mixture from the reactor, and filtration of the catalyst.

Another object of the present invention is the option of continuous mode in a fixed bed reactor to reduce both capital and operation costs.

SUMMARY OF THE INVENTION

Accordingly, the present invention provides a process for the preparation of acyl aromatic ethers useful as important intermediates for drugs and pharmaceuticals, said process comprising reacting an aromatic ether selected from anisole, veratrole and ethyl phenyl ether with an acylating agent selected from C2–C8 acid anhydrides employing nano- or microcrystalline zeolite beta as catalyst, at a temperature in the range of 60–165° C. for a period of 2–24h, and separating the acyl aromatic ethers by a conventional method.

In an embodiment of the invention, the zeolite beta catalyst used is nano or microcrystalline zeolite beta of size ranging between 10 nm to 100 nm and 1 $\mu$m to 50 $\mu$m.

In an embodiment of the invention, the acylating agents used are selected from the group comprising acetic anhydride to benzoic anhydride.

In a further embodiment of the present invention, the reaction in the batch mode is preferably effected at a temperature in the range of 80 to 130° C. for 2–12hrs.

In another embodiment of the present invention acylation is conducted both on a batch mode in a stirred reactor and on a continuous mode in a fixed bed reactor.

In a further embodiment of the invention, the ratio of aromatic ether to acylating agent is from 5:1 to 1:5.

In another embodiment of the invention, the weight of the catalyst is 1 to 50% by weight with respect to the aromatic ether.

DETAILED DESCRIPTION OF THE INVENTION

The novelty of the present invention lies in the use of nanocrystalline or microcrystalline zeolite beta for the acylation of aromatic ethers. Decrease in particle size of zeolite beta, enhances the density of acidic sites and surface area of zeolites, which are essential factors to increase the activity of acylation reaction. As a result of this, the space time yields are increased almost three-fold. This is established in t the experimental section when compared with the results obtained using microcrystalline or zeolite beta as synthesised. Eventually, the capital investment for this process is expected to reduce considerably by 20–30% in view of the higher space time yields. The reaction is also conducted in liquid phase on a continuous mode by pumping a mixture of acetic anhydride and aromatic ethers into a fixed bed packed with microcrystalline zeolite beta in pellet form, while the reaction mixture is continuously withdrawn from the reactor. Three fold enhanced activity is observed in this case. This continuous operation offers further reduction on capital investment and saves the time spent on charging the reactants into the reactor for conducting the reaction, discharging the reaction mixture and filtration of the catalyst practiced in batch mode. This considerably reduces both operating and capital costs.

Scientific Explanation:

In the present invention we have used microcrystalline zeolite beta as a solid acid catalyst for the acylation of aromatic ethers with C2–C8 acid anhydrides, acetic anhydride to benzoic anhydride as acylating agents for the first time.

In the nano and microcrystalline zeolite beta the density of the acidic sites increases because of increased number of broken edges resulted from the broken aluminium silicate rings. The surface area of these particles is also increased due to reduction of the particle size of zeolites. The higher density of acidic sites eventually increases number of acyl cations generated in the reaction in the electrophilic substitution of the Freidel-Crafts acylation and thus enhances activity of the reaction.

Nano crystalline and microcrystalline were prepared as described in example 1 and employed them in the acylation of aromatic ethers with acid anhydrides as acylating agents as described in examples.

The following examples are given by way of illustration of the present invention and therefore should not be construed to limit the scope of the invention.

EXAMPLE 1

Catalyst Preparation a) Zeolite beta:

Tetraethyl orthosilicate and aluminium nitrate of appropriate molar ratios to get desired ratio of Si/Al ranging from 5 to 100 were used. Water is added to tetraethylortho silicate and stirred. To this solution aluminium nitrate, nonahydrate in tetraethylammonium hydroxide solution is added dropwise by a pressure regulating funnel under stirring. After the addition, the solution is kept at 50° C. and later on cooked at 135° C. in an autoclave for one week for crystallization. Then the crystalline solid was filtered and air dried. The resultant solid was calcined at 500° C.

b) Microcrystalline Zeolite Beta-I:

Microcrystalline zeolite beta-1 used in this process was obtained with particle size (1–10 $\mu$m, 95%) by mechanical disintegration of the zeolite beta obtained as described above or by adopting the following synthetic method.

c) Microcrystalline Zeolite Beta-II:

Micro crystalline zeolite beta -II was synthesised with the particle size (5–50 $\mu$m, 85%) by decreasing ageing time to 48 hours instead of one week during the synthesis of zeolite beta according to the above procedure in example 1a.

d) Nanocrystalline Zeolite Beta:

Nanocrystalline zeolite beta synthesised with the particle size (10 nm–100 nm) from the homogenised solution prepared in the first step of zeolite beta (example 1a) which is kept under stirring at different crystallisation times by decreasing ageing time to control the nucleation growth of zeolite during the synthesis. Then the solid was separated by centrifugation, washed with distilled water and dried at 100° C.

EXAMPLE 2

A mixture of anisole (1.5 mol) acetic anhydride (0.75 mol) and zeolite beta (zeolite beta, 20 g) were stirred in a round bottomed flask (1lit) under nitrogen atmosphere at 80° C. After completion of the reaction (followed by G. C.), the reaction mixture was filtered and distilled the reaction mixture to obtain the product. Yield: 108.0 g

EXAMPLE 3

A mixture of anisole (50 mmol), acetic anhydride (10 mmol) and microcrystalline zeolite beta-I (0.25 g) were stirred in a round bottomed flask (50 ml) under nitrogen atmosphere at 80° C. After completion of the reaction (followed by G. C.), the reaction mixture was filtered and distilled the reaction mixture to obtain the product. Yield: 1.47 g

EXAMPLE 4

A mixture of anisole (50 mmol), acetic anhydride (10 mmol) and microcrystalline zeolite beta-II (0.25 g) were stirred in a round bottomed flask (50 ml) under nitrogen atmosphere at 80° C. temperature. After completion of the reaction (followed by G. C.), the reaction mixture was filtered and distilled the reaction mixture to obtain the product. Yield: 1.48 g

EXAMPLE 5

A mixture of anisole and acetic anhydride (2:1 molar solutions were pumped with a flow rate of 3ml/h into a packed bed with the microcrystalline zeolite beta-I (2 g) in a column type reactor from the top at 90° C. The reaction is conducted for 100 hours continuously and the conversion was followed over time by taking aliquots which were analysed by gas chromatography (G. C.). To establish the efficacy of the micronisation process, we have also conducted the acylation reaction under identical conditions with zeolite beta as synthesised and calcined (Zeolyst International and prepared by us). The microcrystalline zeolite beta displayed threefold activity over the samples which are not micronised. The activity remains constant for 100 hours.

EXAMPLE 6

A mixture of veratrole (20 mmol), acetic anhydride (10 mmol) and microcrystalline zeolite beta-I (0.25 g) were stirred in a round bottomed flask (50 ml) under nitrogen atmosphere at 136° C. temperature. After completion of the reaction (followed by G. C.), the reaction mixture was filtered and distilled the reaction mixture to obtain the product. Yield: 1.7 g

EXAMPLE 7

A mixture of anisole (50 mmol), propionic anhydride (10 mmol) and micro-crystaline zeolite beta-I (0.25 g) were stirred in a round bottomed flask (50 ml) under nitrogen atmosphere at 130° C. temperature. After completion of the reaction (followed by G. C.), the reaction mixture was filtered and distilled the reaction mixture to obtain the product. Yield: 1.58 g

EXAMPLE 8

A mixture of anisole (50 mmol), butyric anhydride (10 mmol) and microcrystalline zeolite beta-I (0.25 g) were stirred in a round bottomed flask (50 ml) under nitrogen atmosphere at 130° C. After completion of the reaction (followed by G. C.), the reaction mixture was filtered and distilled the reaction mixture to obtain the product. Yield: 1.7 g

EXAMPLE 9

A mixture of anlsole (40 mmol), valeric anhydride (10 mmol) and microcrystalline zeolite beta-I (0.25 g) were stirred in a round bottomed flask (50 ml) under nitrogen atmosphere at 130° C. After completion of the reaction (followed by G. C.), the reaction mixture was filtered and distilled the reaction mixture to obtain the product. Yield: 1.7 g

EXAMPLE 10

A mixture of anisole (50 mmol), hexanoic anhydride (10 mmol) and microcrystalline zeolite beta-I (0.25 g) were stirred in a round bottomed flask (50 ml) under nitrogen atmosphere at 80° C. After completion of the reaction (followed by G. C.), the reaction mixture was filtered and distilled the reaction mixture to obtain the product. Yield: 1.5 g

EXAMPLE 11

A mixture of anisole (50 mmol), benzoic anhydride (10 mmol) and microcrystalline zeolite beta-I (0.25 g) were stirred in a round bottomed flask (50 ml) under nitrogen atmosphere at 80° C. temperature. After completion of the reaction (followed by G. C.), the reaction mixture was filtered and distilled the reaction mixture to obtain the product. Yield: 1.48 g

TABLE 1

Acylation of anisole with acetic anhydride by zeolite beta catalysts of various particle size

| Example No. | Catalyst (Particle Size) | Time (h) | Isolated yield[a] (%) | STY |
|---|---|---|---|---|
| 2 | Zeolite beta (250–350 μm) | 6 | 98.0 | 0.9 |
| 3 | Microcrystalline beta-I (1–10 μm, 95%) | 2.5 | 99.0 | 2.3 |
| 4 | Microcrystalline beta-II (5–50 μm, 85%) | 2.0 | 99.0 | 2.9 |

[a]based on acetic anhydride; [b]STY = Kg product/Kg cat/h

TABLE 2

Acylation of anisole and veratrole with various acid anhydrides by microcrystalline zeolite beta-I

| Example No. | Acid anhydride | Time (h) | Temp (° C.) | Isolated yields[a] (%) |
|---|---|---|---|---|
| 4 | Acetic anhydride | 2 | 90 | 98 |
| 6 | Acetic anhydride | 6 | 110 | 95[b] |
| 7 | Propionic anhydride | 3 | 90 | 97 |
| 8 | Butyric anhydride | 3 | 130 | 98 |
| 9 | Valeric Anhydride | 3 | 130 | 89 |
| 10 | Hexanoic anhydride | 6 | 130 | 75 |
| 11 | Benzoic anhydride | 6 | 130 | 70 |

[a]based on acetic anhydride. [b]acylation of veratrole.

The main advantages of the present invention are:

1. A novel and ecofriendly process for the preparation of acyl aromatic ethers.

2. The present process eliminates the use of corrosive and stoichiometric quantities of aluminium chloride.

3. Nanocrystalline or microcrystalline zeolite beta have been used as catalysts fox the acylation of aromatic ethers for the first time.

4. The selectivity and the yields are quantitative in case of anisole.

5. The reactions are faster with shorter duration. Work-up procedure is simple.

6. The present process envisages no disposal problem as the catalyst can be used for several cycles. The catalyst was subjected to 4 recycles which displayed consistent activity.

7. The present process is environmentally safe since there is no disposal problem.

8. The process is economical.

9. The productivity (in terms of space time yields) is high.

10. The use of nano- or microcrystalline zeolite beta has enhanced space time yields by three-fold which reduces the capital investment by 20–30%.

11. The option of continuous mode in a fixed bed reactor saves time spent on charging the reactant into the reactor, discharging the reaction mixture and filtration of the catalyst.

12. The option of continuous mode in a fixed bed reactor reduces both capital and operation costs.

What is claimed is:

1. An improved process for the preparation of acyl aromatic ethers useful as important intermediates for drugs and pharmaceuticals, wherein the said process comprises reacting an aromatic ether selected from anisole, veratrole and ethyl phenyl ether with an acylating agent selected from a C2–C8 acid anhydrides, employing nano- or microcrystalline zeolite beta as catalyst, at a temperature in the range of 60–165° C. for a period of 2–24 h, and separating the acyl aromatic ethers by a conventional method.

2. A process as claimed in claim 1 wherein the zeolite beta catalyst used is selected from nano- or microcrystalline zeolite beta of the particle size ranging between 10 nm to 100 nm and 1 $\mu$m to 50 $\mu$m.

3. A process as claimed in claim 1 wherein the acylating agents are selected from the group comprising acetic anhydride to benzoic anhydride.

4. A process as claimed in claim 1 wherein the reaction is conducted in stirred batch reactor or in a continuous fixed bed reactor.

5. A process claimed in claim 4 wherein the reaction in the batch mode is preferably effected at a temperature in the range of 80 to 100° C. for 2–12 hrs.

6. A process as claimed in claim 1 wherein the ratio of aromatic ether to acylating agent is from 5:1 to 1:5.

7. A process as claimed in claim 1 wherein the weight of the catalyst is 1 to 50% by weight with respect to the aromatic ether.

* * * * *